(12) United States Patent
Aubert

(10) Patent No.: US 9,499,481 B2
(45) Date of Patent: Nov. 22, 2016

(54) METHOD FOR PREPARING LACTAMES, COMPRISING A PHOTONITROSATION STEP, FOLLOWED BY A BECKMANN TRANSPOSITION STEP

(71) Applicant: ARKEMA FRANCE, Colombes (FR)

(72) Inventor: Thierry Aubert, Pau (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 14/252,610

(22) Filed: Apr. 14, 2014

(65) Prior Publication Data

US 2014/0246303 A1 Sep. 4, 2014

Related U.S. Application Data

(63) Continuation of application No. 12/993,975, filed as application No. PCT/FR2009/050886 on May 14, 2009, now abandoned.

(30) Foreign Application Priority Data

May 26, 2008 (FR) ..................................... 08 53419

(51) Int. Cl.
*C07D 201/04* (2006.01)
*C07D 227/087* (2006.01)
*C07C 249/06* (2006.01)

(52) U.S. Cl.
CPC ........... *C07D 201/04* (2013.01); *C07C 249/06* (2013.01); *C07D 227/087* (2013.01); *C07C 2101/20* (2013.01)

(58) Field of Classification Search
CPC .................................................. C07D 201/04
USPC ................................................ 540/464, 535
See application file for complete search history.

(56) References Cited

U.S. PATENT DOCUMENTS

| | | |
|---|---|---|
| 3,553,091 A | 1/1971 | Nishikawa et al. |
| 3,652,552 A | 3/1972 | Garritsen et al. |
| 4,211,700 A | 7/1980 | Michel et al. |
| 4,492,365 A | 1/1985 | Desaar |
| 6,194,570 B1 | 2/2001 | Atofina |
| 6,197,999 B1 | 3/2001 | Atofina |
| 2008/0214836 A1 | 9/2008 | Lacroix et al. |
| 2009/0003400 A1 | 1/2009 | Nagahama et al. |

FOREIGN PATENT DOCUMENTS

| | | |
|---|---|---|
| EP | 1995834 | 11/2008 |
| JP | 2000-95756 | 4/2000 |
| JP | 2000-164931 | 6/2000 |
| JP | 2001/002636 | 1/2001 |
| JP | 2001-509472 | 7/2001 |
| JP | 2009-235365 | 10/2009 |
| WO | 01/74758 | 10/2001 |

OTHER PUBLICATIONS

Toyota Motor Corp., Toyota Central R & D Labs Inc., "Polylactic Acid Composite Molding, Manufacturing Method for Polylactic Acid Composite Molding, and Surface Member for Automobile Interior Material," Patent Abstracts of Japan; Oct. 15, 2009; English Abstract of JP 2009-235365.
Sumitomo Electric Ind. Ltd.; "White Color Light Source", Patent Abstracts of Japan; Jun. 16, 2000; English Abstract of JP 2000-164931.
Miyama et al.; "Quantum Yield of Photonitrosation of Cyclohexane in Homogeneous System"; Quantum Yield of Photonitrosation of Cyclohexane; Jun. 30, 1969; pp. 4345-4347.
English Translation of : Hirohito Okino and Katsuhiko Suzuki; "Synthesis of E-Caprolactam Using the TORAY and PNC Methods"; Excerpt from vol. 60, No. 8 of Kagaku Kogyo (The Journal of Chemical Engineering of Japan); Mar. 25, 1996.
Kreisel, G., "Leuchtdioden in der Chemie-Eine Hochzeit verschiedener Technologien", Chemie Ingenieur Technik (2007), 79 (1-2), pp. 153-159.
Matsushita, Y., "Recent Progress on Photoreactions in Microreactors", Pure Appl. Chem., (2007), vol. 79, No. 11, pp. 1959-1968.
Matsushita, Y., "Photocatalytic Reduction in Microreactors", Chemistry Letters, vol. 35, No. 4 (2006), pp. 410-411.
Setoyama, T., "Autocatalytic Beckmann Rearrangement of Cyclohexanone-Oxime in Liquid Phase", Science and Technology in Catalysis 2006, pp. 129-132.
Seeberger, P., "Microreactor Technology", Sigma-Aldrich ChemFiles, vol. 5, No. 7, pp. 1-20.
Ikushima, Y., et al., "Chemical Reaction of Organics in Supercritical Water", Materials Chemistry in Supercritical Fluids, 2005, pp. 123-144.

(Continued)

*Primary Examiner* — Bruck Kifle
(74) *Attorney, Agent, or Firm* — Millen, White, Zelano and Branigan, P.C.

(57) ABSTRACT

The invention relates to a method for preparing lactames, according to which a photonitrosation of a cycloalkane is carried out using nitrosyl chloride (NOCl). According to the invention, said photonitrosation is carried out by means of LEDs emitting a monochromatic light. The method according to the invention can also include a step comprising Beckmann transposition/dechlorination of the oxime hydrochloride generated during said phonitrosation, preferably carried out in a glass microreactor.

11 Claims, No Drawings

(56) References Cited

OTHER PUBLICATIONS

Mao, D., "Influence of Calcination Temperature and Preparation Method of TiO2—ZrO2 on Conversion of Cyclohexanone Oxime to E-Caprolactam over B2O3//TiO2—ZrO2 Catalyst", Applied Catalysis A: General 263 (2004), pp. 83-89.

Ikushima, Y., "Development of Environmentally Friendly Synthetic Process Using Super Critical Water", National Institute of Advanced Industrial Science and Technology, Japan (2004)—Abstract.

Ikushima, Y., "New Production Method for Raw Materials of Synthetic Fibers Employing Supercritical Water. Development of Synthetic Method for E-Caprolactam Without Using Concentrated Sulfuric Acid". National Institute of Advanced Industrial Science and Technology, Japan (2004)—Abstract.

Ikushima, Y., "Innovation in Environmentally Benign Production of E-Caprolactam Using Supercritical Water", National Institute of Advanced Industrial Science and Technology, Japan (2003)—Abstract.

Sato, M., "Acceleration of Chemical Reactions Using a Supercritical Water Microreaction System", International Journal of Chemical Reactor Engineering (2005)—Abstract.

Ikushima, Y., "Innovation in a Chemical Reaction Process Using a Supercritical Water Microreaction System" Environmentally Friendly Production of Vepsin-Caprolactam, Chemical Communications (Cambridge, UK) (2002)—Abstract.

Ichimura et al., "Photoreactions", Microchemical Engineering in Practice, T. R. Dietrich, Ed., Blackwell Publishing (2006), pp. 385-402.

Organikum, VEB Deutscher Verlag der Wissenschaften Berlin, 1988, pp. 576-577.

Puffr et al.; "Lactam-Based Polyamides"; Polymerization, Structure and Properties, vol. I, 1991.

JP 2010-6776 A; Toray Industries, Inc.; Method for Manufacturing Cycloalkanone Oxime and Chemical Reaction Apparatus; English Translation; Jan. 14, 2010.

METHOD FOR PREPARING LACTAMES, COMPRISING A PHOTONITROSATION STEP, FOLLOWED BY A BECKMANN TRANSPOSITION STEP

FIELD OF THE INVENTION

The present invention relates to a process for preparing lactams, comprising, in particular, a step of photonitrosation of cycloalkanes in the presence of light-emitting diodes, referred to as LEDs in the rest of the text, followed by a Beckmann rearrangement step carried out in a microreactor, preferably in a glass microreactor.

PRIOR ART AND TECHNICAL PROBLEM

The industrial usefulness of lactams is known. By way of example, caprolactam and lauryllactam are precursors of polyamides 6 and 12, respectively.

At the industrial level, a process for synthesizing a lactam from a cycloalkane can successively implement the following two reaction steps:

in a first reaction step, a photonitrosation of the cycloalkane is carried out using nitrosyl chloride (NOCl). This photonitrosation is generally carried out in an organic solvent/sulfuric acid two-phase medium using mercury lamps or sodium lamps. An oxime is thus produced in the organic phase and is subsequently extracted in the form of oxime hydrochloride by the sulfuric acid phase;

in a second reaction step, a Beckmann rearrangement of the extracted oxime hydrochloride is carried out in a concentrated sulfuric acid medium so as to obtain the lactam. This lactam resulting from the Beckmann rearrangement is subsequently isolated and purified so as to give a product of high purity.

This type of process is described, for example, in WO200613699, WO9901424, EP 0989118 and U.S. Pat. No. 3,553,091.

It should be noted that this type of process is not most commonly used to produce lactams and that, generally, the Beckmann rearrangement is carried out starting from an oxime obtained from a cycloalkanone and not by photonitrosation of a cycloalkane; consequently, firstly, the oxime is not in hydrochloride form but in "free base" (nonsalified) or sulfate form, and secondly, it does not contain chlorinated impurities resulting from the photonitrosation.

The process described above comprising a photonitrosation step is more rapid, but has drawbacks. For example, the photonitrosation step is particularly expensive.

This is because the mercury or sodium lamps used are fragile and have a short lifetime. In addition, they require a considerable, and therefore expensive, cooling and supply of electricity, given their very high power.

Moreover, this photonitrosation step is not very selective and generates from 5% to 10% of chlorinated derivatives, in particular chlorooxime hydrochlorides, which are extracted by the sulfuric acid together with the desired oxime hydrochloride, and also 5% to 10% of other impurities.

Such chlorinated derivatives are converted—reactions subsequently referred to as dechlorination reactions—during the second reaction step relating to the Beckmann rearrangement, which decreases the yield of this rearrangement.

Thus, the term "dechlorination" is intended to mean any chemical reaction which makes it possible to eliminate the chlorine atom(s) bonded to a carbon backbone.

Specifically, since the temperature and residence time conditions necessary for the dechlorination are more severe than the conditions required to carry out the Beckmann rearrangement, this results in side reactions in which the final lactam and the oxime hydrochloride resulting from the photonitrosation step are hydrolyzed.

For this reason, it is difficult to obtain both a good rearrangement yield and a good dechlorination yield in this second reaction step. Specifically, whatever the conditions of temperature and residence times studied in conventional volume reactors, the maximum yield from rearrangement of the oxime hydrochloride to give lactam is about 90%, for a dechlorination yield of about 70%, it being noted that conditions which result in an increase in the dechlorination yield cause a decrease in the rearrangement yield which is completely unacceptable from an economic point of view.

Furthermore, the residual chlorinated impurities which have not been converted during the dechlorination reaction must be eliminated during subsequent purification steps, said steps being all the more expensive since the amount of chlorinated impurities is large.

It should, moreover, be noted that the Beckmann rearrangement reaction, which is generally carried out in concentrated sulfuric acid at temperatures above 100° C., is extremely exothermic.

This environment is all the more difficult since the hydrochloric acid present in the medium, originating from the oxime hydrochloride and/or given off during the elimination of the chlorinated derivatives, makes the medium extremely corrosive. This second step therefore requires particularly expensive safety materials and devices.

As regards the use of LEDs for carrying out photochemical reactions, the reader will find some prior arts in the following references: "Leuchtdioden in der Chemie—Ein Hochzeit verschiedener Technologien" [light-emitting diodes in chemistry—a marriage of different technologies] Chemie Ingenieur Technik (2007), 79(1-2), 153-159 or "Recent progress on photoreactions in microreactors", Pure and Applied Chemistry, 79(11), 1959-1968 (2007), or else the studies by the team of Professor Teijiro Ichimura, which focus on the use of LEDs in the ultraviolet range for carrying out various chemical reactions (mainly reduction, N-alkylation and oxidation); see, for example: Chemistry Letters, Vol. 35 No. 4 (2006) p. 410 or "Photoreactions" in "Microchemical Engineering in Practice", T. R. Dietrich, Ed. Blackwell Publishing (2006).

As regards more particularly the use of microreactors, patent WO0174758 describes the use of a microreactor for the Beckmann rearrangement of acetophenone oxime (free base); in this case, there are no dechlorination reactions to be carried out simultaneously with the Beckmann rearrangement, and it is therefore easy to optimize the reaction yield.

The article Studies in Surface Science and Catalysis (2007), 172 (Science and Technology in Catalysis 2006), 129-132, describes a kinetic study of the Beckmann rearrangement of the oxime (free base) in a microreactor; in this case also, there are no dechlorination reactions to be carried out simultaneously with the Beckmann rearrangement.

The rearrangement of cyclohexane oxime (free base) in a metal microreactor is described in the article *Organikum*, VEB Deutscher Verlag der Wissenschaften Berlin, 1988, 576, and also in Chemfiles, Vol. 5, No. 7, publication by Sigma Aldrich; here again, there are no dechlorination reactions to be carried out simultaneously with the Beckmann rearrangement, and it is therefore easy to optimize the reaction yield; moreover, the rearrangement of a mixture of oxime hydrochlorides and of chorooximes, which generates large amounts of corrosive hydrochloric acid, cannot be carried out in metal materials.

Several articles written by the National Institute of Advanced Industrial Science and Technology (Materials Chemistry in Supercritical Fluids (2005), 123-144, CA: 146:358239; International Journal of Chemical Reactor Engineering (2005), 3, No pp. given, CA: 144:88591; Gurin Kemisutori Shirizu (2004), 3 (Chorinkai Ryutai no Saishin Oyo Gijutsu), 45-67, CA: 142:410655; Kurin Tekunoroji (2004), 14(6), 47-50, CA: 141:123911; Petrotech (Tokyo, Japan) (2003), 26(9), 721-725, CA: 140:423523; Chemical Communications (Cambridge, United Kingdom) (2002), (19), 2208-2209, CA: 138:73570) describes the use of microreactors for the rearrangement of cyclohexanone oxime (free base) in a supercritical $H_2O$ medium, and therefore under extreme temperature and pressure conditions. This technology is not applicable to the rearrangement of the oxime hydrochloride resulting from a photonitrosation step, which is in solution in concentrated sulfuric acid.

Finally, the rearrangement of cyclohexanone oxime (free base) in a metal microreactor comprising a fixed-bed $B_2O_3$/$TiO_2$—$ZrO_2$ catalyst is described in Applied Catalysis, A: General (2004), 263(1), 83-89; this method is also not applicable to the rearrangement of a mixture of oxime hydrochloride and chlorooximes, since the hydrochloric acid generated is incompatible with the catalyst used and the material of the microreactor.

BRIEF DESCRIPTION OF THE INVENTION

The present invention relates to a process for preparing lactams, in which a photonitrosation of a cycloalkane is carried out using nitrosyl chloride (NOCl), this photonitrosation being carried out by means of LEDs emitting a monochromatic light. The combination of several LEDs of various wavelengths is not excluded in the context of the invention, provided that each of the LEDs has a monochromatic emission spectrum.

The use of LEDs has many advantages; in particular, said use is less expensive than the use of mercury or sodium lamps. This is because LEDs have a longer lifetime than the lifetime of these lamps and require less cooling and energy consumption.

In addition, LEDs do not contain any mercury, which is an extremely toxic product, the use and the complex recycling of which further increases the cost of use.

LEDs also have the advantage of being a source of monochromatic light, with a relatively narrow emission spectrum, thereby making it possible to improve, surprisingly, the selectivity of the photonitrosation reaction.

For example, the use of LEDs having a wavelength of 590 nm makes it possible to increase the selectivity for the photonitrosation reaction by 1 to 2%.

The process according to the invention can also have one or more of the characteristics below, considered individually or according to all the combinations technically possible:
according to one embodiment, the monochromatic light emitted by the LEDs has an average wavelength value included in a range between 550 and 650 nm;
according to one embodiment, the monochromatic light emitted by the LEDs has an average wavelength value of from 585 to 595 nm;
according to another embodiment, a microreactor, the body of which is preferably made of glass, is used to carry out the photonitrosation of the cycloalkane;
according to another embodiment, the process according to the invention also comprises a step of Beckmann rearrangement of the oxime hydrochloride generated during this photonitrosation;
according to one variant, a microreactor is used to carry out the Beckmann rearrangement step, it being possible for the body of the microreactor to advantageously comprise tantalum, a fluoropolymer, a glass steel or glass, said body preferably being made of glass.

It is specified that the term "body of the microreactor" is intended to mean the part of the reactor which is in contact with the reaction medium, of the photonitrosation step and/or of the Beckmann rearrangement step.

According to a second, independent aspect, the invention also relates to a process for preparing lactams, comprising a step of Beckmann rearrangement of an oxime hydrochloride generated during a prior photonitrosation of a cycloalkane and of simultaneous dechlorination, subsequently denoted Beckmann rearrangement/dechlorination, in which a microreactor, the body of which comprises tantalum, a fluoropolymer, a glass steel or glass, is used to carry out this Beckmann rearrangement/dechlorination.

By virtue of this second aspect of the invention, it is possible to carry out Beckmann rearrangements/dechlorinations under conditions for precise control of flow rate, of temperature and of residence time of the reactants, which increases the safety and the yield of this reaction.

In particular, it has been noted that, surprisingly, the dechlorination yield and the Beckmann rearrangement yield are simultaneously improved, independently of the conditions for carrying out the prior cycloalkane photonitrosation step, whether said conditions use LEDs or mercury or sodium lamps of the prior art.

In addition, the use of a microreactor makes it possible to provide optimum safety conditions owing to the small volumes of reactants used and to the excellent control of the exothermicity of the reaction.

According to a more particularly preferred aspect, use is made of a microreactor made of glass, which is less expensive.

Other characteristics and advantages of the invention will become apparent on reading the description of an embodiment of the invention indicated below by way of nonlimiting illustration.

DETAILED DESCRIPTION OF AN EMBODIMENT OF THE INVENTION

A process for preparing lactams in accordance with the invention comprises the use of LEDs for carrying out the photonitrosation of a cycloalkane, followed by a Beckmann rearrangement/dechlorination step carried out in a microreactor, preferably in a glass microreactor.

The term "microreactor" will subsequently be used for any assembly of microstructured reactors mounted in series or in parallel, and the term "microstructured reactors" or simply "microstructure" will subsequently be used for any chemical reactor, at least one of the characteristic dimensions of which is between 1 micron and 15 millimeters and which is characterized by:
an extremely high value, compared with the conventional volume reactors, of the ratio between its internal surface area and its internal volume, more specifically of about 1000 $m^2$ $m^{-3}$ or more, compared with generally 100 $m^2$ $m^{-3}$ or less for the conventional reactors;
a very small total internal volume, generally between a few microliters and a few tens of milliliters;
short characteristic times (residence time, mixing time, etc.), generally less than approximately 10 minutes;

As previously indicated, the use of LEDs makes it possible to reduce the cost of the process of preparing lactams, given their small consumption and their long lifetime compared with mercury or sodium lamps.

In addition, the LEDs have a size and a power which allow them to be used in a microreactor for increasing the selectivity of reactions.

The LEDs used in this embodiment have an electric power of greater than approximately 1 Watt and are characterized by a luminous efficacy of greater than 10 lumens/W.

Such LEDs are available from many suppliers, such as Philips Lumileds (Luxeon® range, for example), Cree Inc. or Nichia Corporation.

Moreover, the use of a microreactor allows homogeneous stirring of the reactive medium and provides, in particular, better transfer of the oxime hydrochloride from the organic phase to the sulfuric acid phase.

Finally, controlling the reaction temperature and the residence time of the chemical compounds present is easier in a microreactor, which is an advantage for a highly exothermic reaction such as Beckmann rearrangement.

Advantageously, at least one of the two steps, on the one hand photonitrosation and, on the other hand, Beckmann rearrangement/dechlorination, is carried out in such a microreactor.

In one preferred embodiment of the invention, each of the two reaction steps, on the one hand photonitrosation and, on the other hand, Beckmann rearrangement/dechlorination, is carried out in such a microreactor.

As regards the first reaction step, the photonitrosation of a cycloalkane is carried out using nitrosyl chloride (NOCl). This photonitrosation is carried out in an organic solvent/sulfuric acid two-phase medium under temperature and concentration conditions well known to those skilled in the art, such as those described, for example, in document EP 0 993 438.

An oxime is thus generated in an organic phase, this oxime being subsequently extracted in the form of oxime hydrochloride by the sulfuric acid phase.

According to one preferred form of the invention, the cycloalkane is cyclododecane; cyclododecanone oxime hydrochloride is then obtained by photonitrosation, according to the reaction:

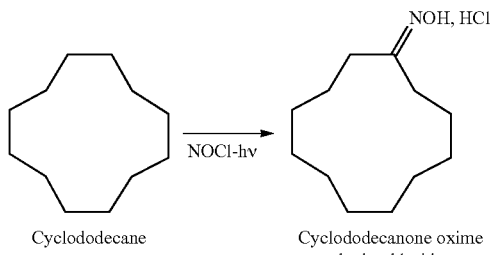

Cyclododecane     Cyclododecanone oxime hydrochloride

It should be noted that, in accordance with the invention, the source of photons (hν) consists of LEDs which emit monochromatically, i.e. mainly according to a wavelength range or spectrum which is significantly narrower than the emission range of mercury or sodium lamps, typically about 15 to 30 nm.

Consequently, this LED emission spectrum is characterized by an average wavelength having a value which is typically in a range of from 550 to 650 nm in the case of the photonitrosation carried out in accordance with the invention.

Thus, an average wavelength value may be from 585 to 595 nm.

In addition, the use of a microreactor allows better spatial distribution of the photons emitted by the LEDs in the reaction medium, which is an advantage for a photochemical reaction such as photonitrosation.

As regards the second reaction step, a Beckmann rearrangement/dechlorination of the oxime hydrochloride resulting from the first, photonitrosation step is carried out in a concentrated sulfuric acid medium.

Continuing the preferred form of the invention above, of a preparation of lactam starting from cyclododecane, lauryllactam or dodecalactam is obtained according to the reaction:

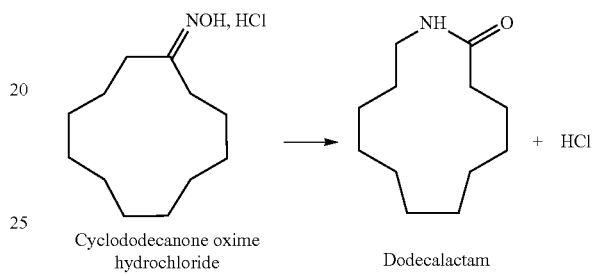

Cyclododecanone oxime hydrochloride     Dodecalactam

Unexpectedly, the use of microreactors for the Beckmann rearrangement/dechlorination step allows a surprising improvement in both the yield from dechlorination and the yield from Beckmann rearrangement per se, by virtue of the precise control of the temperatures and the residence times, which makes it possible to significantly reduce the side reactions (hydrolysis of the oxime hydrochloride and of the lactam).

Thus, it is possible to achieve dechlorination yields of between 70% and 80% and Beckmann rearrangement yields of greater than 90%, which was not possible when carrying out this reaction in conventional volume reactors.

These unexpected results can be obtained, for example, under the following conditions:
 either in a single reaction step carried out at temperatures of between 160 and 230° C. and residence times of between 2 seconds and 10 minutes according to the number of microreactors combined,
 or in two reaction steps: the first, corresponding in the majority to the Beckmann rearrangement, being carried out at temperatures of between 100 and 160° C. and residence times of between 2 seconds and 10 minutes according to the number of reactors combined; the second, corresponding in the majority to the dechlorination reactions, being carried out at temperatures of between 160 and 240° C. and residence times of between 2 seconds and 8 minutes according to the number of microreactors combined.

Moreover, the use of microreactors markedly improves the safety of the process owing to the small volumes used and to the particularly precise control of the exothermicity.

The steps described above—Beckmann rearrangement and dechlorination—are advantageously carried out in a glass microreactor. This is because the use of glass as material makes it possible to solve the problems of corrosion usually observed with conventional materials such as metals.

It should be noted here that the use of a microreactor requires investments which are compensated for by an improvement in the yields of the various reactions for the synthesis of lactams described above—photonitrosation and/or Beckmann rearrangement and dechlorination.

Similarly, the decrease in the problems associated with corrosion, with safety and with the high costs of these operations compensates for these investments.

The technology for manufacturing these glass microreactors is today well known to those skilled in the art, and a glass microreactor supplied, for example, by the companies Corning or Invenios can be used to carry out the above reactions.

Typically, the microreactors used can be in the form of a plate of which the surface area is between 100 and 2500 $cm^2$; they have channels of which the diameter is between 50 microns and 10 mm and a system of heating by means of a heat-transfer fluid which makes it possible to achieve temperatures that can reach 250° C.

All types of glasses can be used to manufacture these microreactors, such as borosilicate glasses (Pyrex®, for example), soda-lime glasses, lead glasses, silica glasses or glass-ceramics.

EXAMPLES

Example 1

Photonitrosation of Cyclododocane by Means of LEDs 3806 g of a solution containing 32% by mass of cyclododecane in carbon tetrachloride and 200 g of sulfuric acid at 90% are introduced, with stirring, into a two-liter reactor equipped at its center with a bundle of 80 Luxeon LXML-PL01-0030 LEDs from the company Philips Lumileds, each supplying 30 lumens (for a current of 350 mA) and emitting a monochromatic light centered at 590 nm, the lamps are turned on, and then 10 l/h of anhydrous hydrochloric acid gas and 10 l/h of nitrosyl chloride are introduced continuously for 3 h, while cooling the reaction medium such that the temperature does not exceed 25° C.

The selectivity of the reaction, expressed by the ratio of the percentage of cyclododecanone oxime to the sum of the percentage of cyclododecanone oxime and of by-products of the reaction, assayed by HPLC in the sulfuric acid phase, is 89%, and therefore greater than that observed when using the mercury-vapor or sodium-vapor lamps of the prior art.

Example 2

Beckmann Rearrangement/Dechlorination

90% sulfuric acid is injected, at a flow rate of 1 l/h and at ambient temperature, with a Grundfos DME-2-18 feed pump into a microstructure of "DT" type having an internal volume of 9 ml (reactive circuit), manufactured by the company Corning and described, for example, in the article: Chem. Eng. Technol. 2008, 31, No. 8, 1146-1154 by P. Barthe et al.

The heat-transfer fluid circuit is injected, at a flow rate of 6 l/min, with oil which is at 205° C. by means of a Lauda Integral XT 350 HW bath. Once the temperature of 200° C. has been reached at the outlet of the microstructure in the heat-transfer fluid circuit, the injection of sulfuric acid is stopped and a solution containing 30.1% (by mass) of cyclododecanone oxime (determined by HPLC) in 90% sulfuric acid is injected at a flow rate of approximately 2.5 l/h by means of two Grundfos DME-2-18 pumps mounted in parallel.

After 25 minutes during which 1017.9 g of oxime solution have been injected, 964.8 g of a brown lactam solution are recovered at the outlet of the reactive circuit, the HPLC analysis of said lactam solution being as follows:

Lactam: 30.2% (by mass).

The rearrangement yield is therefore 95.1%.

The chlorine percentages in the solid lactams and oximes obtained by precipitation and washing of the sulfuric solutions of oxime and of lactam are, respectively, 2.18% and 0.65%; the dechlorination yield is therefore 70%.

Example 3

Beckmann Rearrangement/Dechlorination

90% sulfuric acid is injected, at a flow rate of 1 l/h and at ambient temperature, with a Grundfos DME-2-18 feed pump, into 4 microstructures, mounted in series, of "DT" type; each having an internal volume of 9 ml (reactive circuit), manufactured by the company Corning and described, for example, in the article Chem. Eng. Technol. 2008, 31, No. 8, 1146-1154 by P. Barthe et al.

The heat-transfer fluid circuit is injected, at a flow rate of 6 l/min, with oil which is at 190° C. by means of a Lauda Integral XT 350 HW bath. Once the temperature of 185° C. has been reached at the outlet of the microstructure in the heat-transfer fluid circuit, the injection of sulfuric acid is stopped and a solution containing 30.9% (by mass) of cyclododecanone oxime (determined by HPLC) in 90% sulfuric acid is injected at a flow rate of approximately 1 l/h by means of 1 Grundfos DME-2-18 pump.

After 1 hour during which 766 g of oxime solution have been injected, 738 g of a brown lactam solution are recovered at the outlet of the reactive circuit, the HPLC analysis of said lactam solution being as follows:

Lactam: 29.3% (by mass).

The rearrangement yield is therefore 91.3%.

The chlorine percentages in the solid lactams and oximes obtained by precipitation and washing of the sulfuric solutions of oxime and of lactam are, respectively, 2.62% and 0.48%; the dechlorination yield is therefore 81.7%.

The use of microreactors therefore shows that, compared with the prior art, an improvement in the Beckmann rearrangement yield (95.1% compared with 90% in the prior art), for a dechlorination yield of 70%, or an improvement in the dechlorination (81.7% compared with 70% in the prior art), for a Beckmann rearrangement yield of 91.3%, are observed.

The invention claimed is:

1. In a process for preparing lauryllactam or caprolactam from oximes, comprising photonitrosating of a cycloalkane using nitrosyl chloride (NOCl), the improvement wherein said photonitrosating is carried out by exposing the cycloalkane to LEDs emitting a monochromatic light.

2. The process as claimed in claim 1, in which the cycloalkane is cyclododecane.

3. The process as claimed in claim 1, wherein the monochromatic light emitted by the LEDs has an average wavelength value included in a range from 550 to 650 nm.

4. The process as claimed in claim 3, wherein the monochromatic light emitted by the LEDs has an average wavelength value of from 585 to 595 nm.

5. The process as claimed in claim 1, wherein a microreactor is used to carry out the photonitrosation of the cycloalkane.

6. The process as claimed in claim 5, wherein the body of the microreactor is made of glass.

7. The process as claimed in claim 1, wherein the lactam is prepared from the oxime by Beckmann rearrangement/dechlorination of the oxime hydrochloride generated during photonitrosation, and a microreactor is used to carry out a Beckmann rearrangement/dechlorination step.

8. The process as claimed in claim 7, wherein the body of the microreactor comprises tantalum, a fluoropolymer, a glass steel or glass.

9. A process for preparing lauryllactam or caprolactam, comprising preparing an oxime by photonitrosation of a cycloalkane using nitrosyl chloride in the presence of LEDs emitting monochromatic light, and subjecting oxime hydrochloride generated during photonitrosation to Beckman rearrangement/dechlorination to produce lauryllactam or caprolactam.

10. The process as claimed in claim 9, in which the cycloalkane is cyclododecane.

11. The process as claimed in claim 9, wherein the body of the microreactor is made of glass.

* * * * *